(12) United States Patent
Kase

(10) Patent No.: US 11,633,305 B2
(45) Date of Patent: Apr. 25, 2023

(54) TAPING KIT AND METHOD FOR ATTACHING TAPE TO BE AFFIXED TO BODY

(71) Applicant: KINESIO IP LLC, Albuquerque, NM (US)

(72) Inventor: Kenzo Kase, Tokyo (JP)

(73) Assignee: KINESIO IP LLC, Albuquerque, NM (US)

( * ) Notice: Subject to any disclaimer, the term of this patent is extended or adjusted under 35 U.S.C. 154(b) by 211 days.

(21) Appl. No.: 16/627,870

(22) PCT Filed: Jul. 6, 2018

(86) PCT No.: PCT/JP2018/025694
§ 371 (c)(1),
(2) Date: Dec. 31, 2019

(87) PCT Pub. No.: WO2019/009411
PCT Pub. Date: Jan. 10, 2019

(65) Prior Publication Data
US 2020/0121514 A1 Apr. 23, 2020

(30) Foreign Application Priority Data
Jul. 6, 2017 (JP) ............................... JP2017132729

(51) Int. Cl.
*A61F 13/00* (2006.01)
*A61F 13/02* (2006.01)

(52) U.S. Cl.
CPC .... *A61F 13/0253* (2013.01); *A61F 13/00063* (2013.01); *A61F 13/0206* (2013.01);
(Continued)

(58) Field of Classification Search
None
See application file for complete search history.

(56) References Cited

U.S. PATENT DOCUMENTS 4,999,235 A 3/1991 Lunn et al.
D625,825 S * 10/2010 Arbesman .................... D24/190
(Continued)

FOREIGN PATENT DOCUMENTS

CN 102 178 580 A 9/2011
CN 204839931 U 12/2015
(Continued)

OTHER PUBLICATIONS

Kinesiology Taping Application for Shoulder Impingement (https://vimeo.com/130055152) (Year: 2015).*
(Continued)

*Primary Examiner* — Kim M Lewis
(74) *Attorney, Agent, or Firm* — IP Business Solutions, LLC

(57) ABSTRACT

A taping kit is capable of controlling a depth of a stimulation according to the purpose to structural parts from the epidermis to the dermis and fascia. The taping kit includes two or more tapes to be affixed to the body containing at least a stretchable substrate and an adhesive layer on one surface of the substrate. The taping kit includes a first tape which has a plurality of slits in a longitudinal direction, and a second tape which has a plurality of slits in a longitudinal direction and is overlapped and attached on at least a part of the first tape.

2 Claims, 21 Drawing Sheets

(52) U.S. Cl.
CPC ... *A61F 13/0273* (2013.01); *A61F 2013/0028* (2013.01); *A61F 2013/00646* (2013.01)

(56) References Cited

U.S. PATENT DOCUMENTS

| | | | | |
|---|---|---|---|---|
| D625,826 | S | * 10/2010 | Arbesman | .................... D24/190 |
| 7,951,443 | B2 | 5/2011 | Esaki | |
| D649,255 | S | * 11/2011 | Kase | ................. A61F 13/00085 |
| | | | | D24/190 |
| D691,276 | S | * 10/2013 | Bushby | ................. A61F 13/024 |
| | | | | D24/190 |
| D743,566 | S | * 11/2015 | Arbesman | ......... A61F 13/00059 |
| | | | | D24/190 |
| 9,833,351 | B2 | * 12/2017 | Arbesman | ......... A61F 13/00059 |
| 2009/0104402 | A1 | * 4/2009 | Esaki | ................. A61F 13/0269 |
| | | | | 428/136 |
| 2010/0016771 | A1 | * 1/2010 | Arbesman | ............. A61F 13/066 |
| | | | | 602/5 |
| 2010/0312160 | A1 | 12/2010 | Creighton et al. | |
| 2016/0106595 | A1 | * 4/2016 | Arbesman | ......... A61F 13/00085 |
| | | | | 602/54 |
| 2016/0242950 | A1 | 8/2016 | Chase | |
| 2017/0049629 | A1 | * 2/2017 | Arbesman | ............. A61F 13/024 |

FOREIGN PATENT DOCUMENTS

| | | |
|---|---|---|
| EP | 3 067 023 A1 | 9/2016 |
| JP | H01-43253 A | 2/1989 |
| JP | H07-16258 A | 1/1995 |
| JP | H10-33741 A | 2/1998 |
| JP | 2001-245920 A | 9/2001 |
| JP | 2002-233545 A | 8/2002 |
| JP | 2002-238944 A | 8/2002 |
| JP | 2009-28137 A | 2/2009 |
| KR | 2009-0060867 A | 6/2009 |
| KR | 2011-0004638 U | 5/2011 |
| WO | 2014/190416 A1 | 12/2014 |

OTHER PUBLICATIONS

Chinese Office Action mailed by Chinese Patent Office dated Apr. 8, 2021 in corresponding Chinese patent application No. 201880045108.9.

International Search Report issued for the International Application of this national phase application (US) dated Jul. 25, 2018.

Written Opinion of the International Searching Authority issued for the International Application of this national phase application (US) dated Jul. 25, 2018.

Extended European search report mailed by European Patent Office dated Jul. 16, 2021 in corresponding European patent application No. 18828070.5-1102.

Russian Office Action mailed by Russian Patent Office dated Aug. 9, 2021 in corresponding Russian patent application No. 2020104287/14 (006646).

* cited by examiner

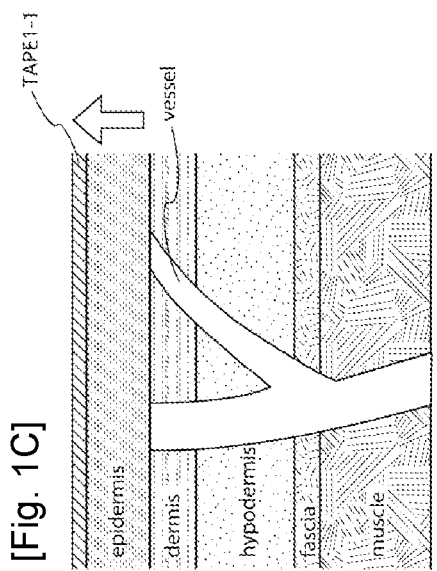
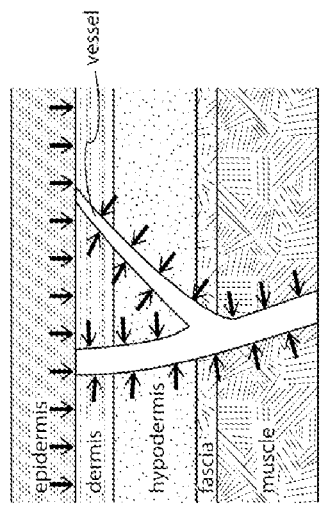
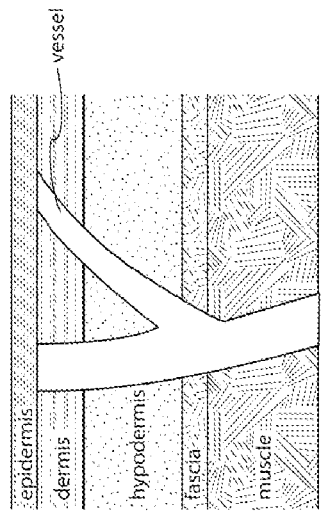

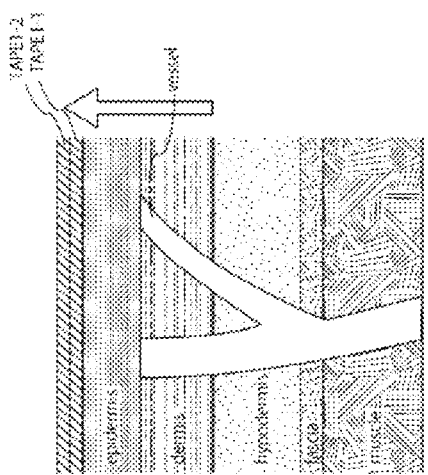
[Fig. 2A]
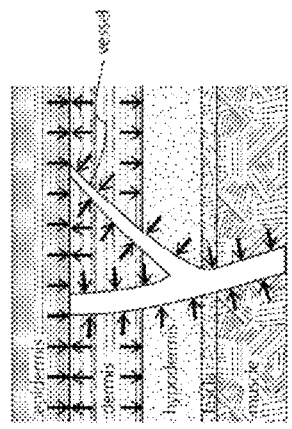
[Fig. 2B]
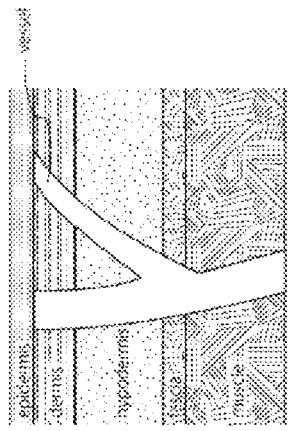
[Fig. 2C]

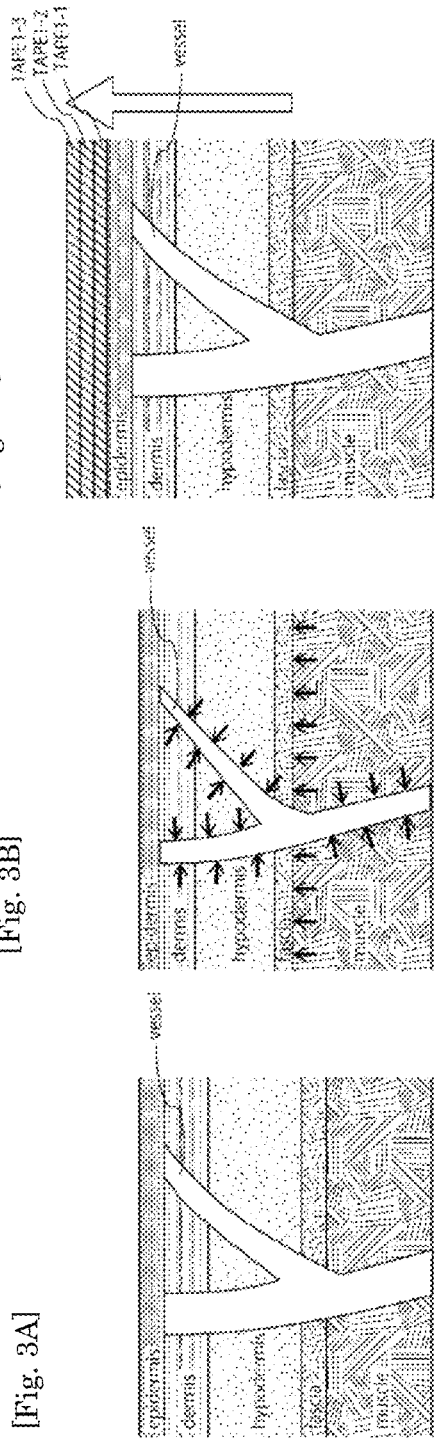

[Fig. 4]
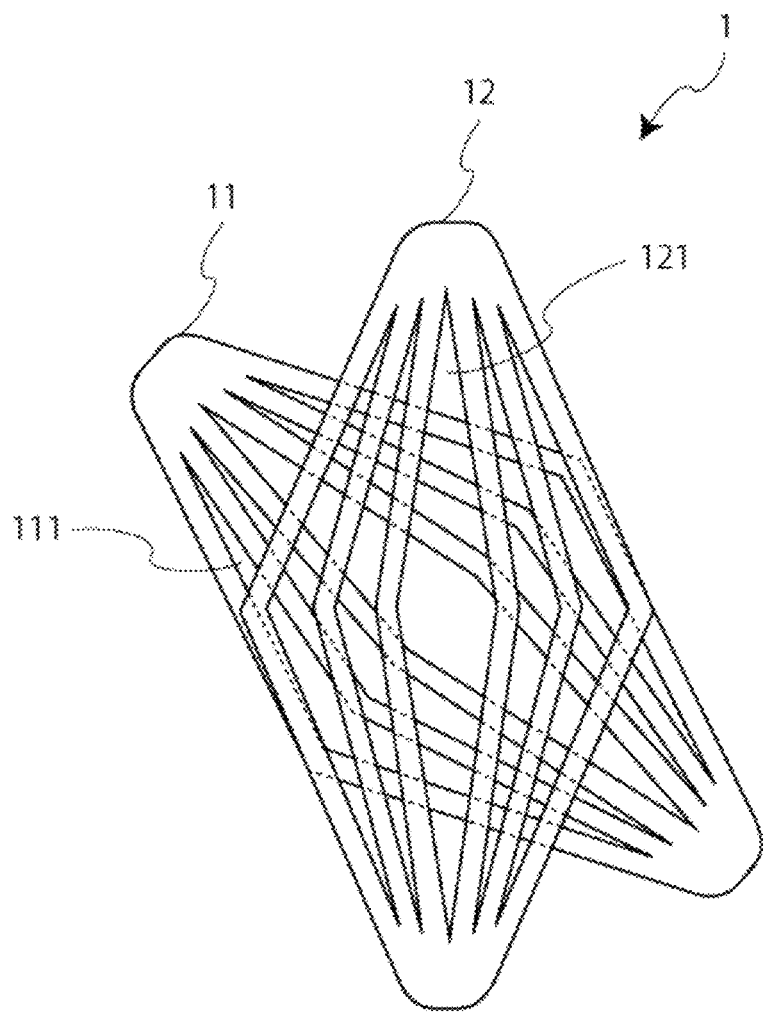

[Fig. 5]
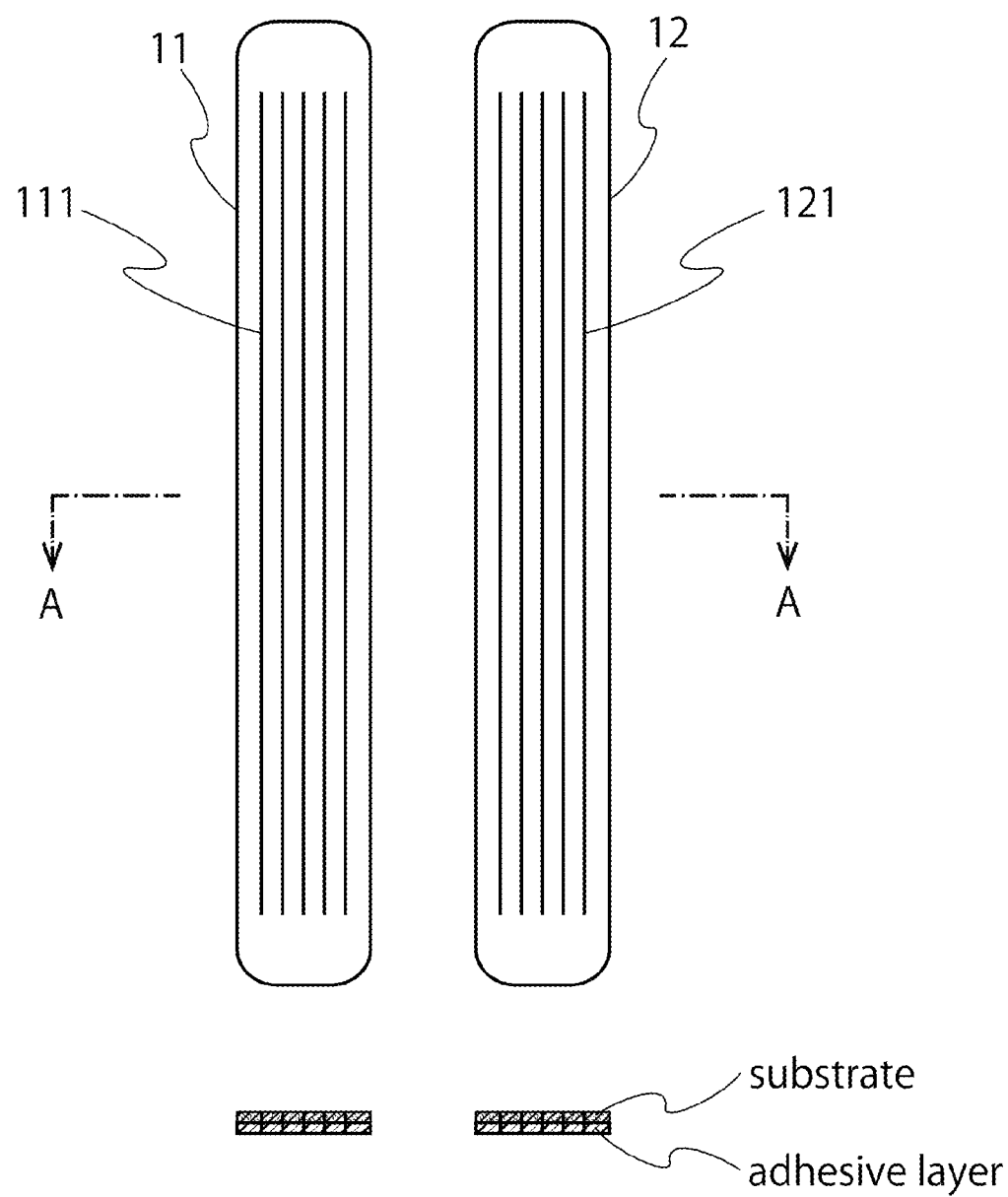

[Fig. 6]
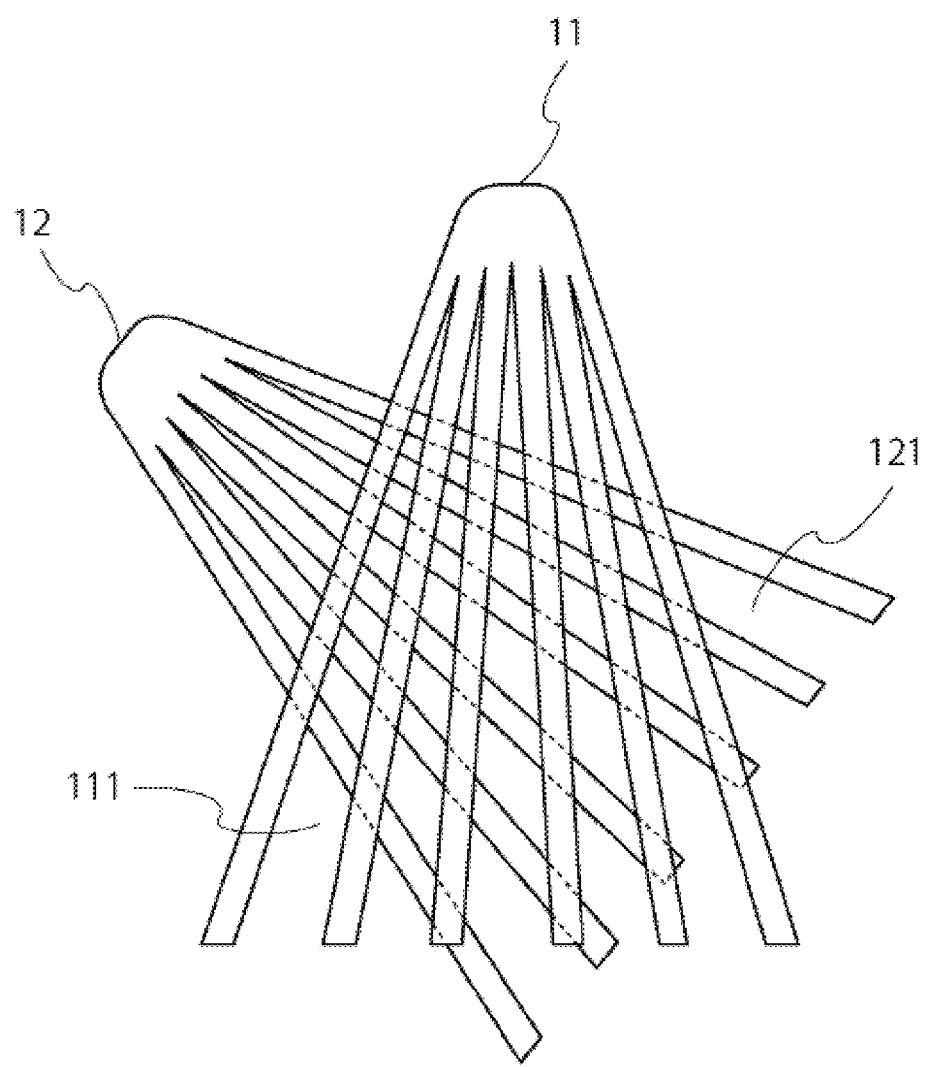

[Fig. 7]
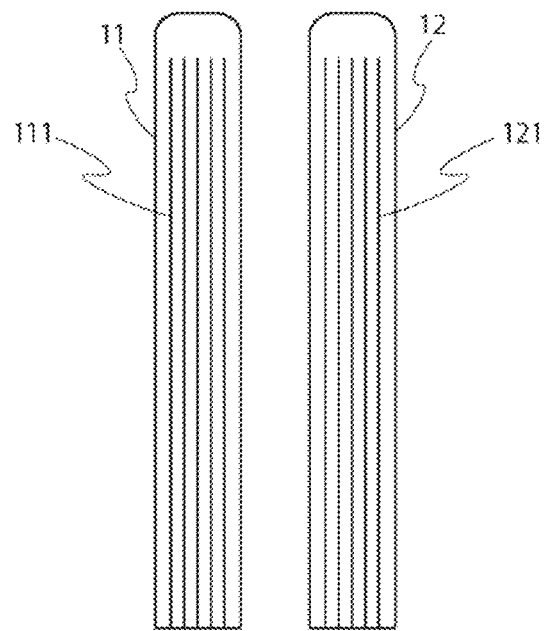
[Fig. 8]
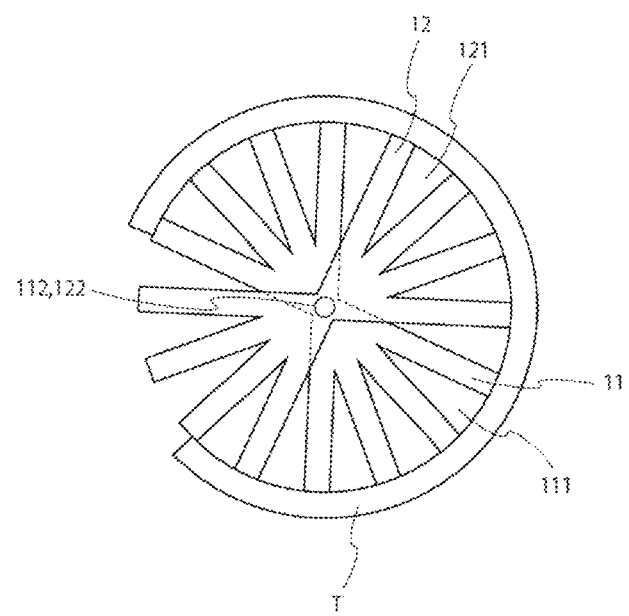

[Fig. 9]
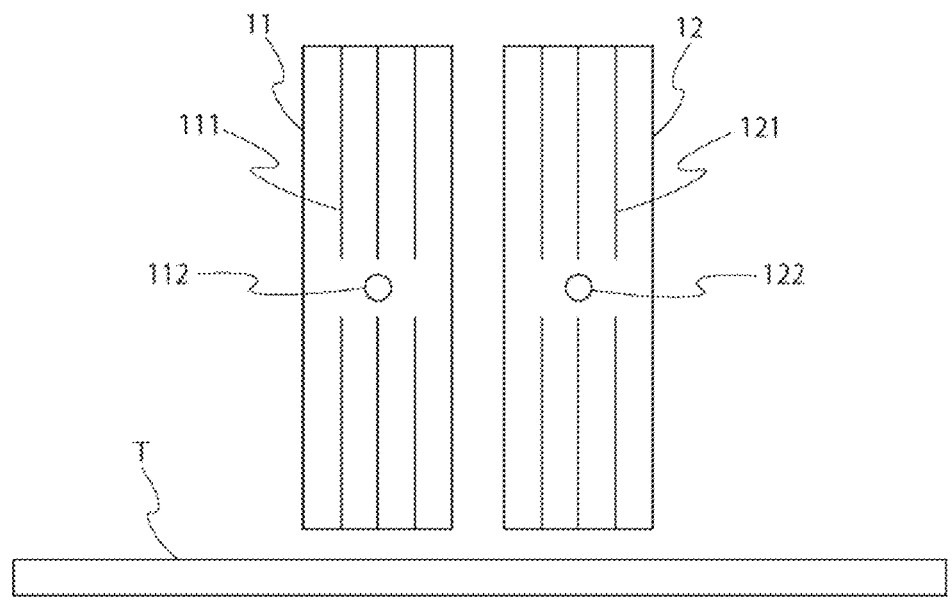
[Fig. 10]
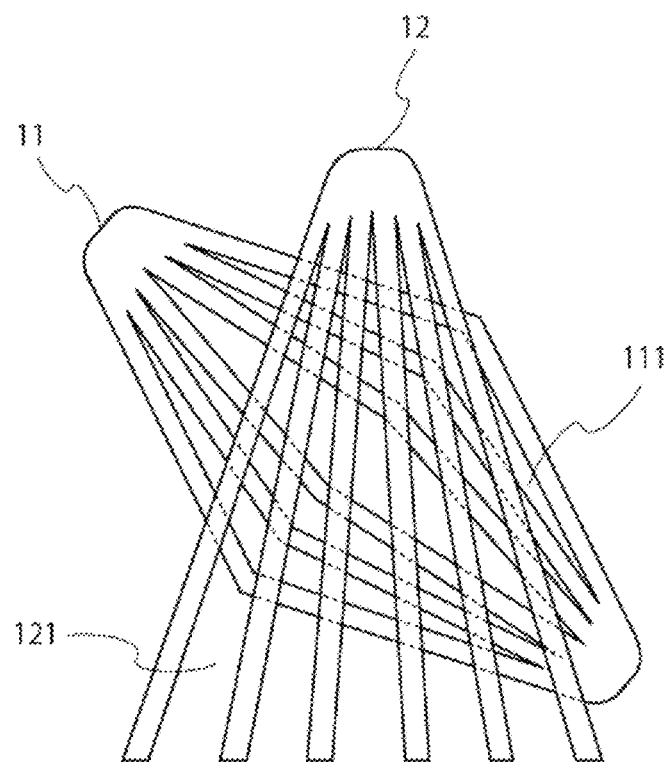

[Fig. 11]
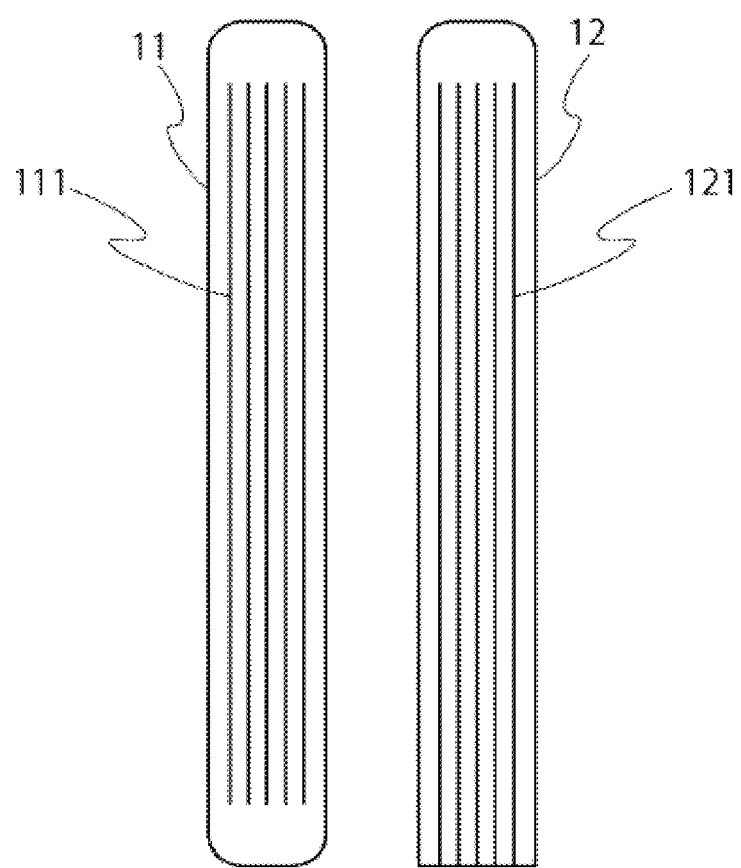

[Fig. 12]
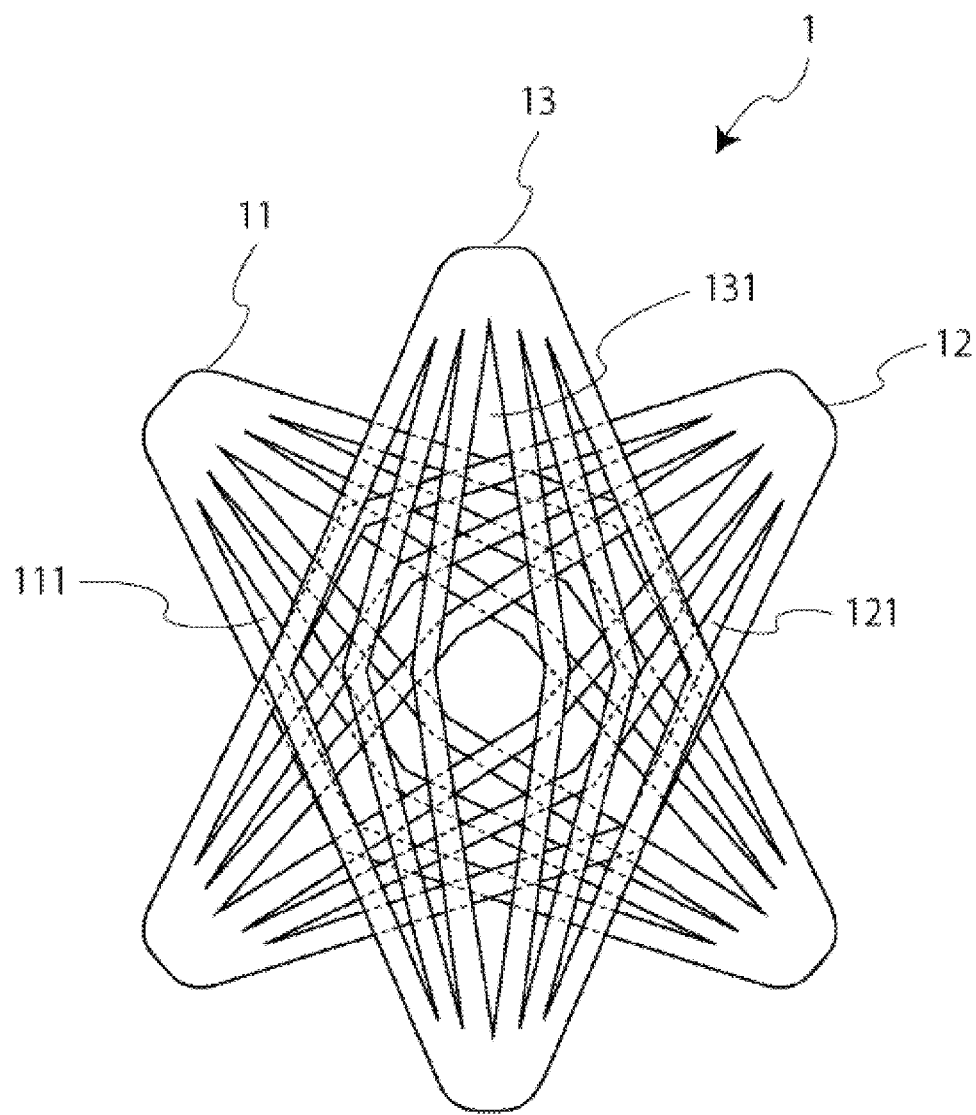

[Fig. 13]
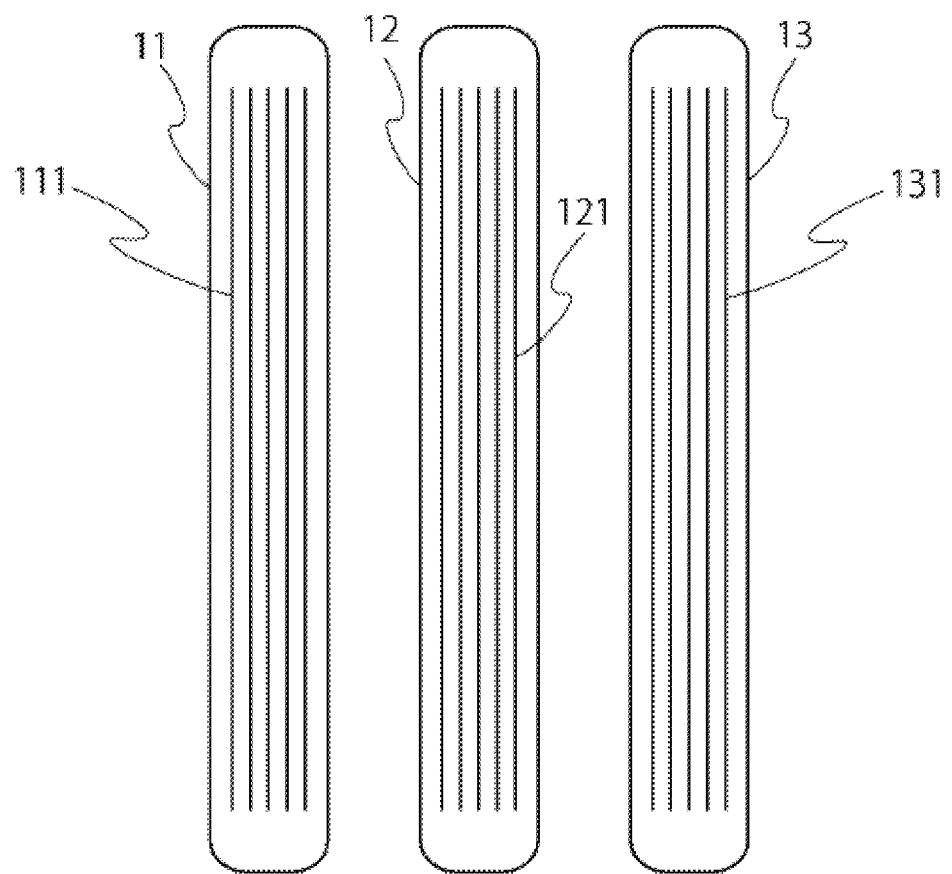

[Fig. 14]
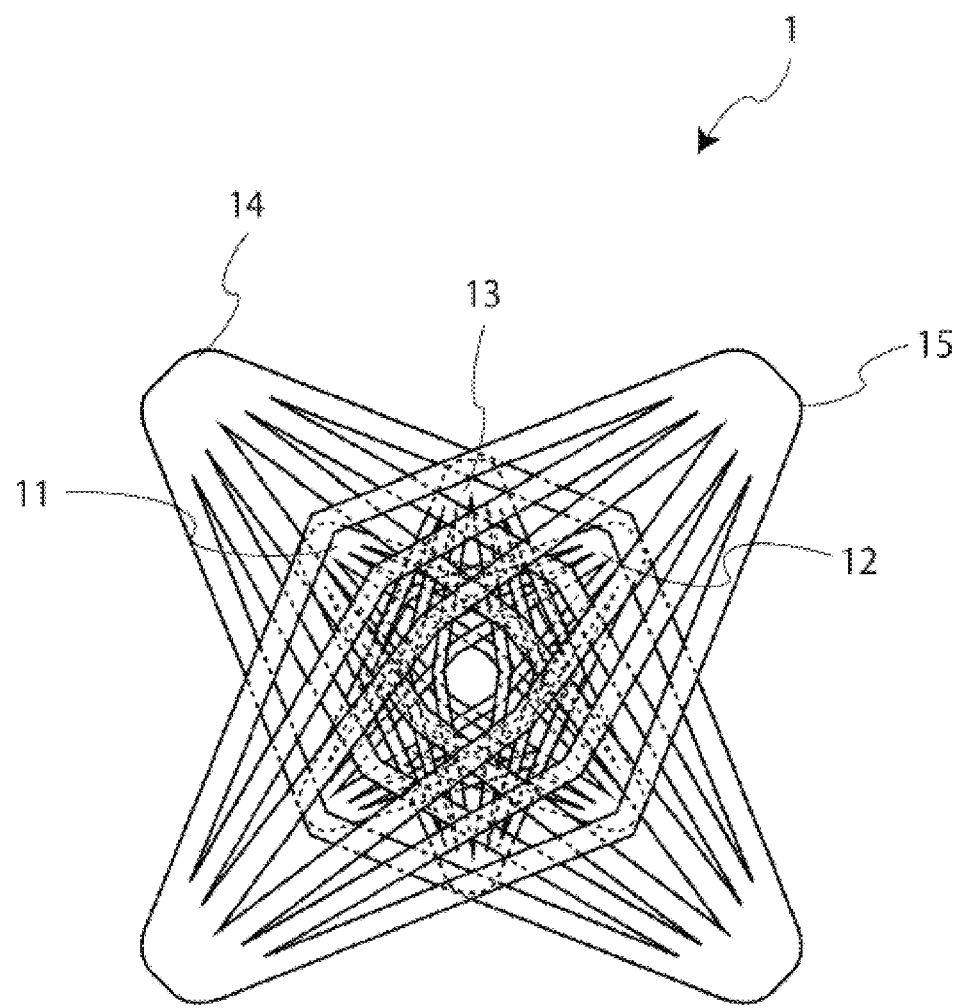

[Fig. 15]
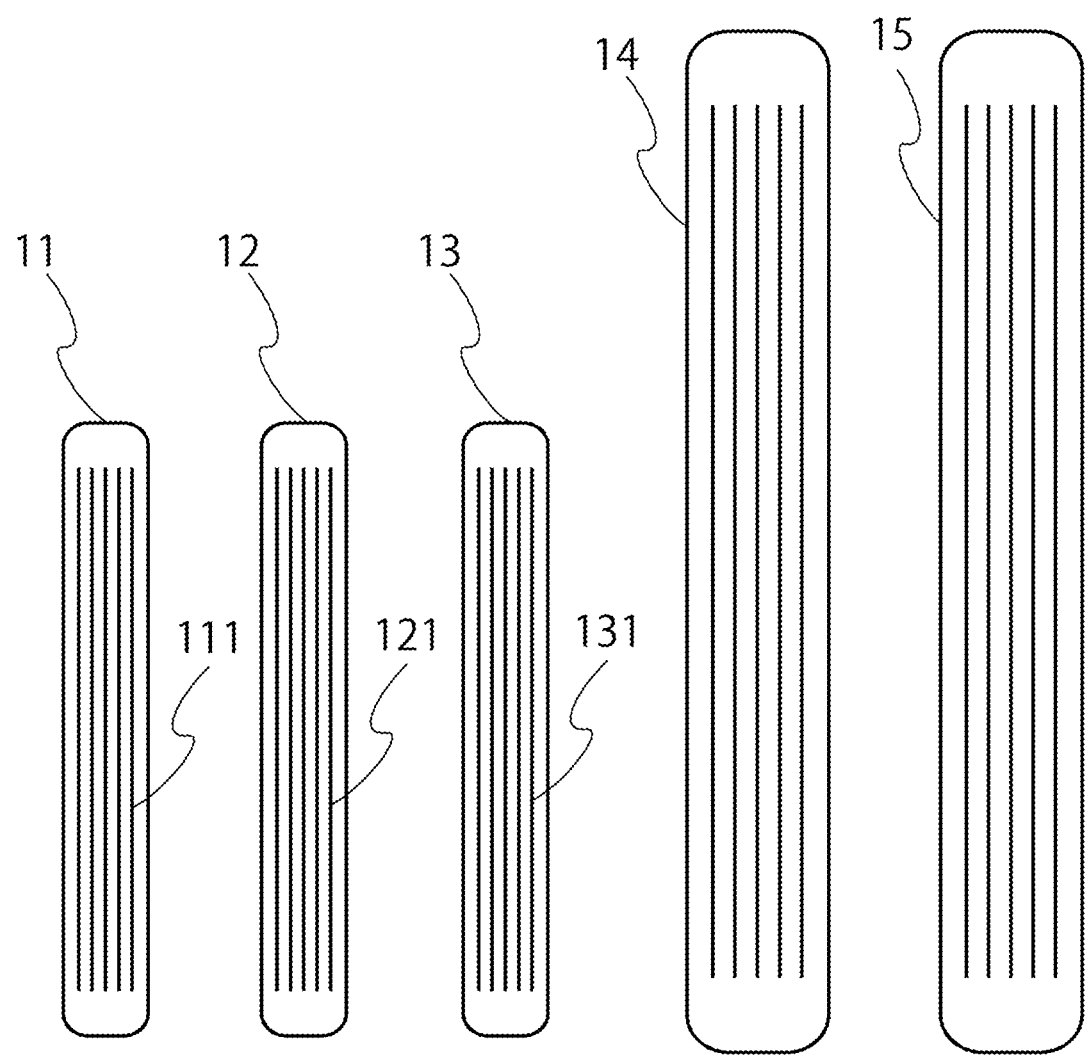

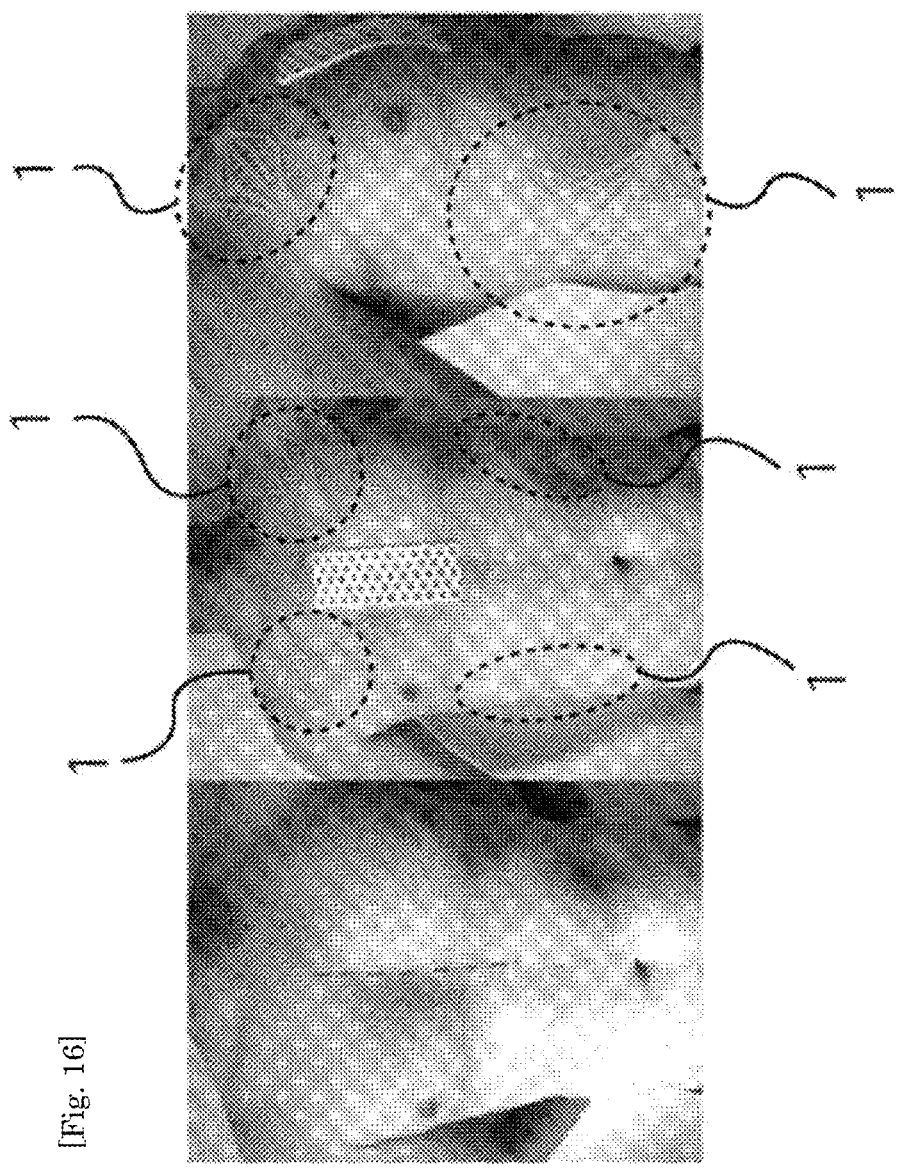
[Fig. 16]

[Fig. 17]
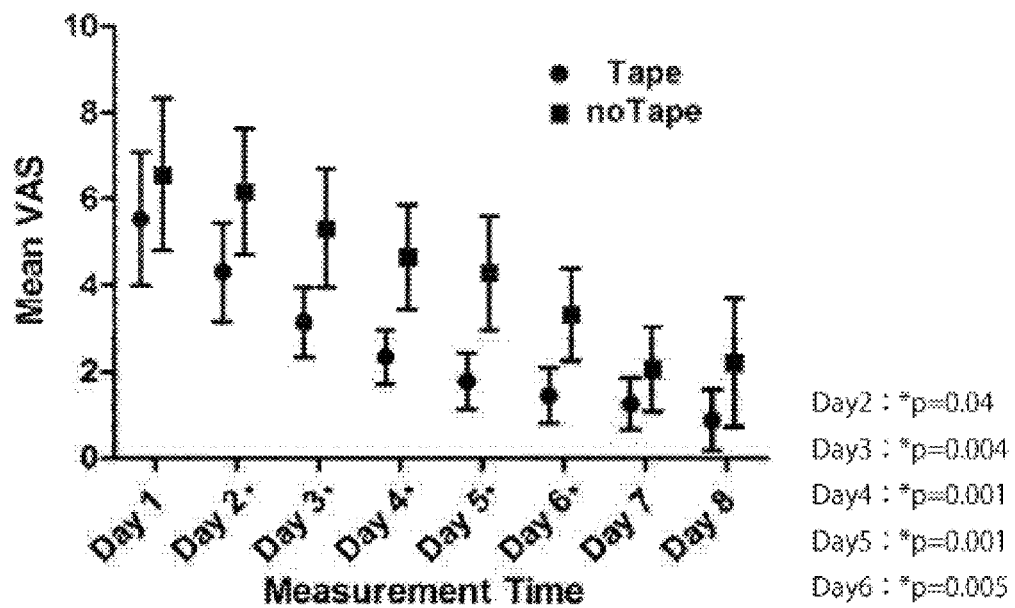
[Fig. 18]
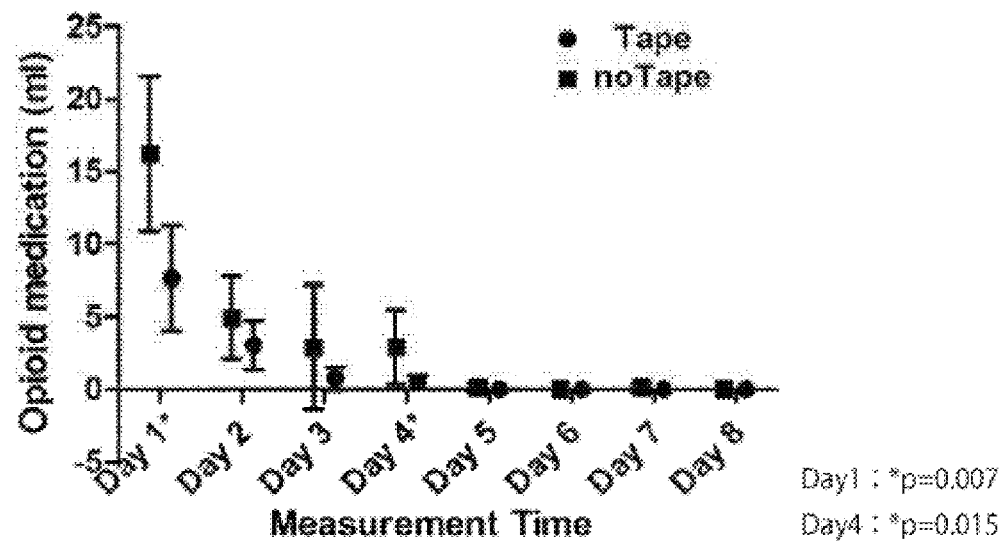

[Fig. 19]
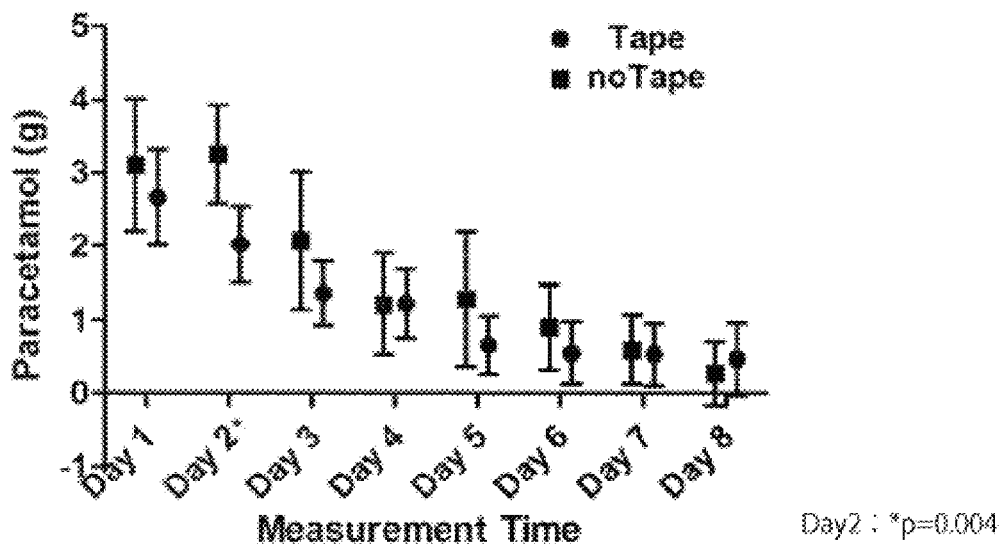
[Fig. 20]
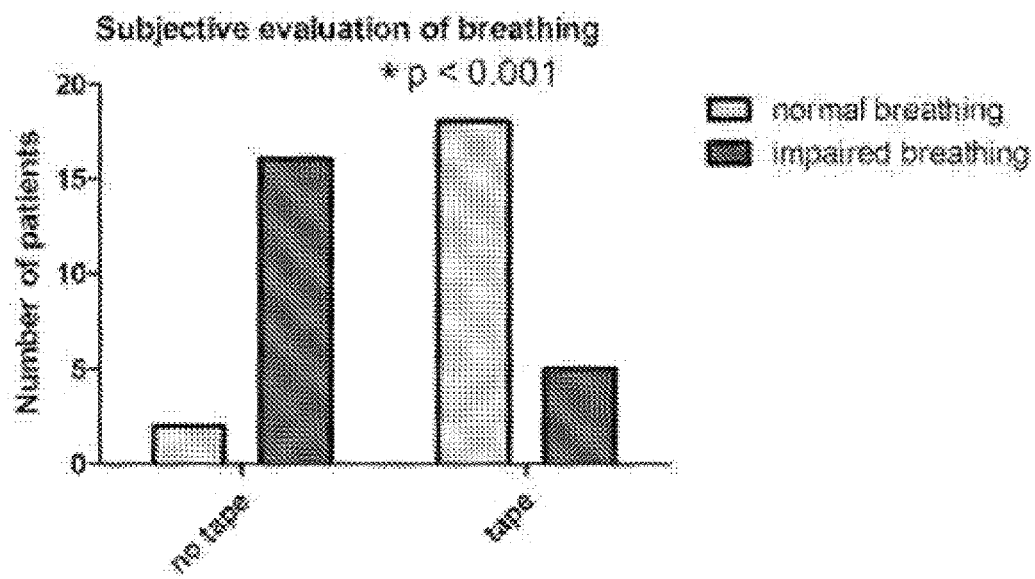

[Fig. 21]
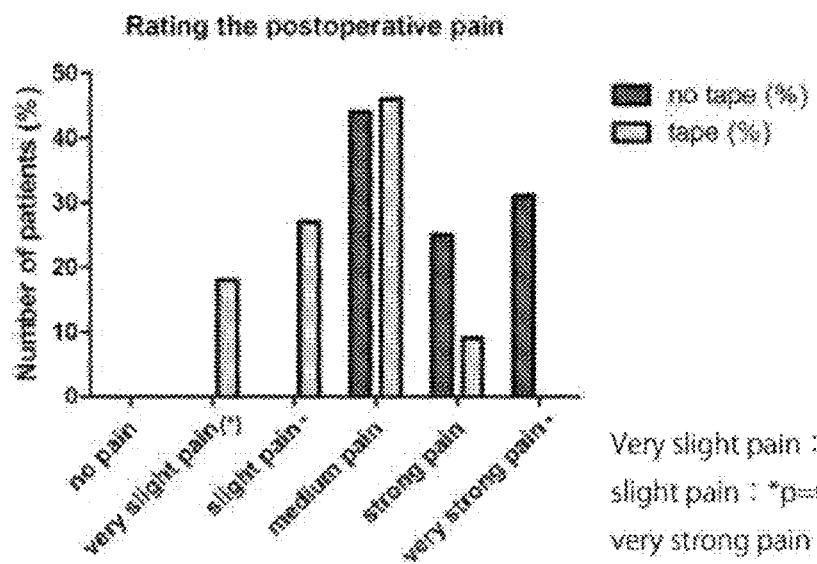
[Fig. 22]
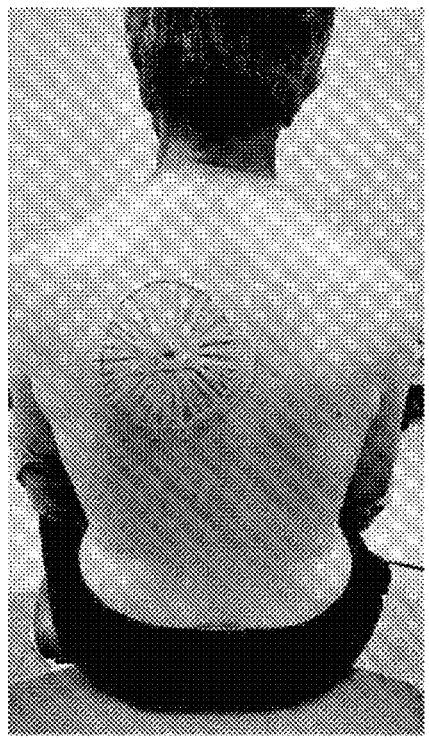

[Fig. 23]
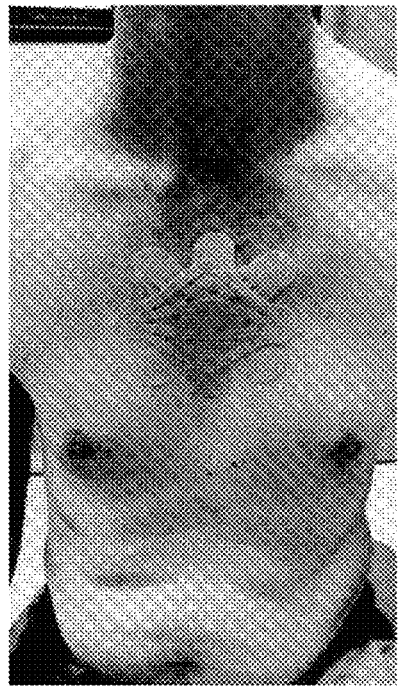
[Fig. 24]
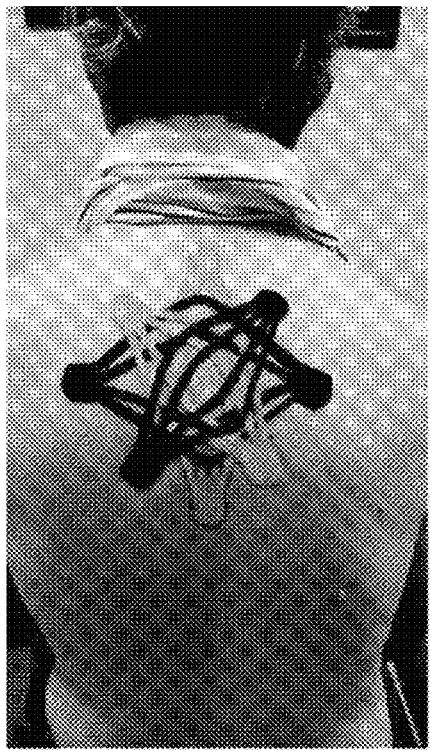

[Fig. 25]
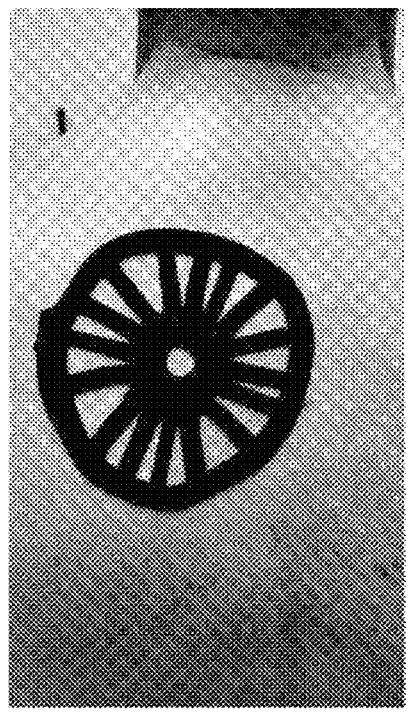
[Fig. 26]
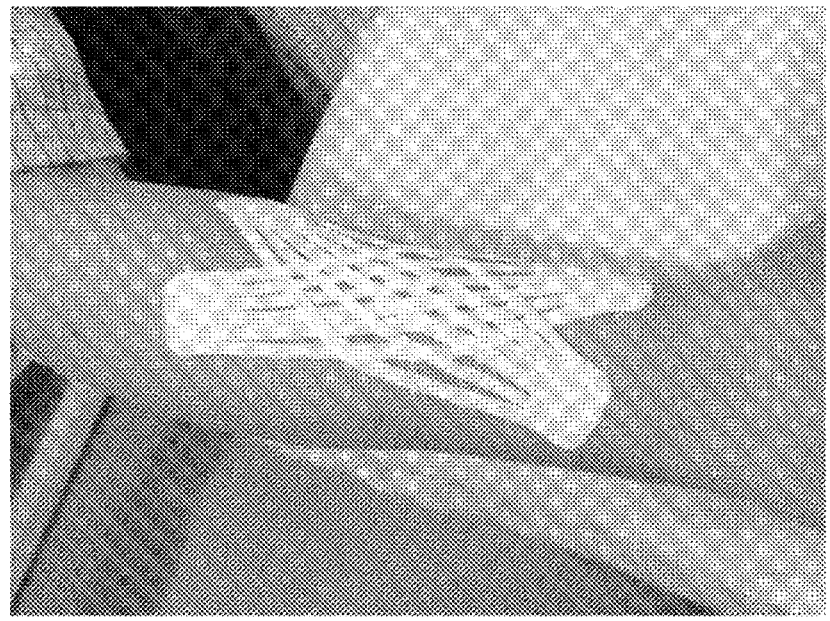

[Fig. 27]

[Fig. 28]
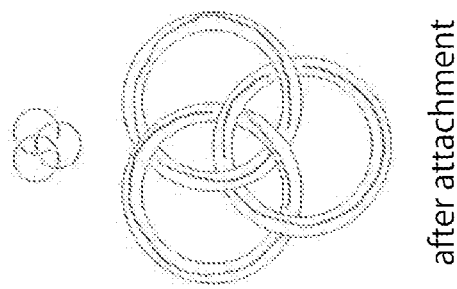
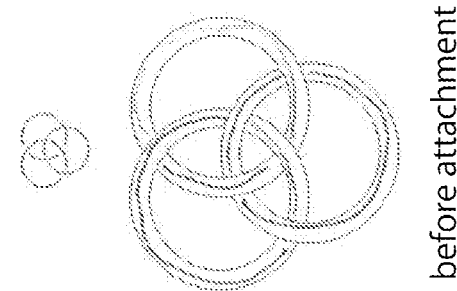
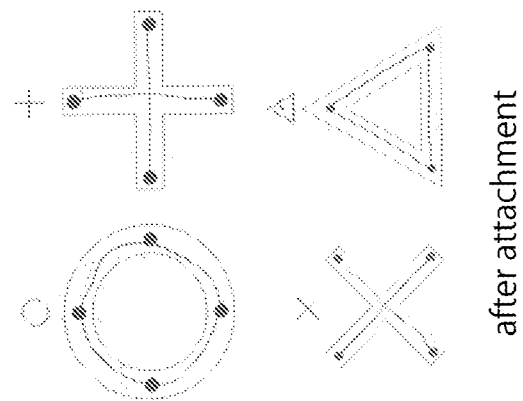
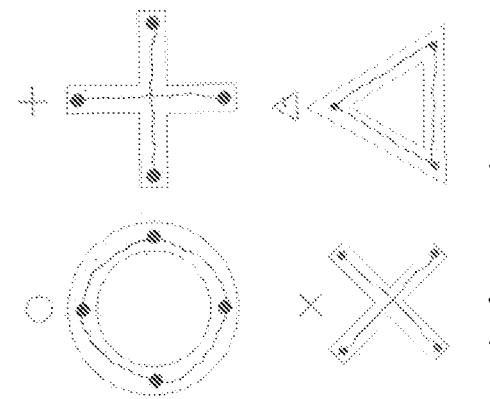

TAPING KIT AND METHOD FOR ATTACHING TAPE TO BE AFFIXED TO BODY

TECHNICAL FIELD

The present invention relates to a taping kit comprising two or more tapes to be affixed to the body; more particularly relates to a taping kit affecting the epidermis, dermis, fascia, and the like, and a method for attaching a tape to be affixed to the body.

BACKGROUND ART

These days, tapes have been utilized in fields of folk remedies, correction of distortion of meridian, stimulation of acupuncture points, slimming, function recovery of the fascia or muscle, function recovery of bones or joints, correction of tendon positions, body massage, body incubation, body protection, reduction of stiffness such as shoulder stiffness, pain or inflammation, taping, cosmetic, and therapy of affected parts on the body.

The tapes to be affixed to the body are improved in a material, a form and a function, in order to exhibit the desired effects described above. For example, some tapes to be affixed to the body having an improved shape or form of an adhesive layer have been proposed.

Patent Document 1 discloses a tape capable of providing stimulation without straining the skin by the tape attached on an affected part. The tape is characterized in that multiple slit parts extending in a longitudinal direction of the tape are formed in a width direction of the tape.

Patent Document 2 discloses a tape having the same functions as those of the tape in Patent Document 1, and the tape has slit parts having a predetermined length and facing a longitudinal direction of the tape are intermittently formed throughout a width direction.

Patent Document 3 discloses a tape which is difficult to be peeled off on sweating and is air-permeable. The tape has a structure in which winding, linear gaps having exposing folds of a substrate are formed on an adhesive layer.

Patent Document 4 discloses a tape effective for shoulder stiffness, headache, menstrual pain, joint pain, or muscular pain. The tape is characterized by containing two adhesive layers, and separating a space between a first adhesive layer and a second adhesive layer in a predetermined distance.

CITATION LIST

Patent Document

Patent Document 1: JP-A No. 2002-238944
Patent Document 2: JP-A No. 2002-233545
Patent Document 3: JP-A No. H10-033741
Patent Document 4: JP-A No. 2001-245920

SUMMARY OF THE INVENTION

Technical Problem

The present invention mainly aims at providing a taping kit capable of controlling a depth of stimulation to structural parts from the epidermis to the dermis and fascia depending on the purpose.

Solution to Problem

The present invention, first, provides a taping kit comprising: two or more tapes to be affixed to the body containing at least a stretchable substrate and an adhesive layer on one surface of the substrate, which comprises
a first tape which has a plurality of slits in a longitudinal direction, and
a second tape which has a plurality of slits in a longitudinal direction and is overlapped and attached on at least a part of the first tape.

In the taping kit according to the present invention, wherein the slits in the first tape can be provided inside in the longitudinal direction while leaving both of the end parts in the longitudinal direction.

In the taping kit according to the present invention, wherein the slits in the second tape can also be provided inside in the longitudinal direction while leaving both of the end parts in the longitudinal direction.

The taping kit according to the present invention can further comprise a third tape which has a plurality of slits in a longitudinal direction, and is overlapped and attached on at least a part of the first tape and the second tape.

In such a case, the slits in the third tape can also be provided inside in the longitudinal direction while leaving both of the end parts in the longitudinal direction.

The taping kit according to the present invention can be used for attaching to the skin after an incision.

Next, the present invention provides a method for attaching tapes to be affixed to the body, which contains at least a stretchable substrate and an adhesive layer on one surface of the substrate, comprises:
a first attaching step in which a first tape, which has a plurality of slits in a longitudinal direction, is attached to an affected part; and
a second attaching step in which a second tape, which has a plurality of slits in the longitudinal direction, is overlapped and attached on at least a part of the first tape.

The attaching method of the present invention can be applied to the skin after an incision.

Advantageous Effects of the Invention

According to the present invention, the depth of the stimulation can be controlled to the structure part from the epidermis to the dermis and the fascia according to the purpose.

BRIEF DESCRIPTION OF DRAWINGS

FIG. 1A is a schematic view showing a normal internal structure.

FIG. 1B is a schematic view showing a state in which the epidermis causes inflammation and swells.

FIG. 1C is a schematic view showing a skin internal structure when one tape to be affixed to the body in a taping kit is attached to a body.

FIG. 2A is a schematic view showing a schematic view showing a normal internal structure.

FIG. 2B is a schematic view showing a state in which the epidermis and dermis cause inflammation.

FIG. 2C is a schematic view showing a skin internal structure when two tapes to be affixed to the body in a taping kit is attached to a body.

FIG. 3A is a schematic view showing a normal internal structure.

FIG. 3B is a schematic view showing a state in which the muscle causes inflammation and swells.

FIG. 3C is a schematic view showing a skin internal structure when three tapes to be affixed to the body in a taping kit is attached to a body.

FIG. 4 is a schematic view when a taping kit according to a first embodiment is attached to a body.

FIG. 5 is a schematic view before the taping kit according to the first embodiment is attached to a body.

FIG. 6 is a schematic view when a taping kit according to a second embodiment is attached to a body.

FIG. 7 is a schematic view before the taping kit according to the second embodiment is attached to a body.

FIG. 8 is a schematic view when a taping kit according to a third embodiment is attached to a body.

FIG. 9 is a schematic view before the taping kit according to the third embodiment is attached to a body.

FIG. 10 is a schematic view when a taping kit according to a fourth embodiment is attached to a body, which is a schematic view showing a taping kit according to the fourth embodiment.

FIG. 11 is a schematic view before the taping kit according to the fourth embodiment is attached to a body.

FIG. 12 is a schematic view when a taping kit according to a fifth embodiment is attached to a body.

FIG. 13 is a schematic view before the taping kit according to the fifth embodiment is attached to a body.

FIG. 14 is a schematic view when a taping kit according to a sixth embodiment is attached to a body.

FIG. 15 is a schematic view before the taping kit according to the sixth embodiment is attached to a body.

FIG. 16 is a photograph that substitutes for a drawing showing a method for attaching a tape in Experimental Example 1.

FIG. 17 is a graph that substitutes for a drawing showing results of pain values in Experimental Example 1.

FIG. 18 is a graph that substitutes for a drawing showing results of amounts of an opioid analgesic used in Experimental Example 1.

FIG. 19 is a graph that substitutes for a drawing showing results of amounts of paracetamol (analgesic) used in Experimental Example 1.

FIG. 20 is a graph that substitutes for a drawing showing the number of occurrences of a subjective symptom of respiratory distress in Experimental Example 1.

FIG. 21 is a graph that substitutes for a drawing showing the number of patients when a degree of pain is divided into 6 classes in Experimental Example 1.

FIG. 22 is a photograph that substitutes for a drawing showing a method for attaching a tape in Experimental Example 2.

FIG. 23 is a photograph that substitutes for a drawing showing a method for attaching a tape in Experimental Example 2.

FIG. 24 is a photograph that substitutes for a drawing showing a method for attaching a tape in Experimental Example 2.

FIG. 25 is a photograph that substitutes for a drawing showing a method for attaching a tape in Experimental Example 2.

FIG. 26 is a photograph that substitutes for a drawing showing a method for attaching a tape in Experimental Example 3.

FIG. 27 is a photograph that substitutes for a drawing showing a method for attaching a tape in Experimental Example 3.

FIG. 28 is a photograph that substitutes for a drawing showing results of a written examination in Experimental Example 3.

DESCRIPTION OF EMBODIMENTS

Preferable embodiments for carrying out the present invention are explained below. Note that the embodiment explained below shows only one example of typical embodiments of the present invention, and the scope of the present invention should not be narrowly interpreted thereby.

<Taping Kit>

First, a skin internal structure is explained when a tape in a taping kit 1 of the present disclosure is attached to a body. FIG. 1 is a schematic view explaining a skin internal structure when one tape to be affixed to the body in the taping kit is attached to a body. Note that, in FIG. 1, a blood vessel is depicted extremely thick for convenience of explanation (hereinafter the same). FIG. 1A shows a normal internal structure, FIG. 1B shows a state in which the epidermis causes inflammation and swells. There are circulation vessels of body fluid such as capillary blood vessels and lymphatic vessels and nerves in the skin. When the epidermis part causes the inflammation and swells, for example, the dermis, subcutaneous tissues, fascia and muscles, and circulation vessels of body fluid and nerves existing therein are compressed, and the circulation of body fluid is stagnated or pain is caused. When one tape 11 to be affixed to the body is attached to the skin, the epidermis is raised as shown in FIG. 1C, then the dermis, the subcutaneous tissue, the fascia and the muscle, and the circulation vessels of body fluid and the nerves existing therein are released from the compression, and the circulation of the body fluid such as blood and lymph is improved. Consequently, the pain is reduced and the healing of the inflammation is facilitated.

FIG. 2 is a schematic view explaining a skin internal structure when two tapes to be affixed to the body in a taping kit are attached to a body. FIG. 2A shows a normal internal structure, and FIG. 2B shows a state in which the epidermis and dermis cause inflammation and swell. For example, when the epidermis and dermis parts cause inflammation and swell, as in FIG. 1 described above, the dermis, subcutaneous tissue, fascia and muscle, and circulation vessels of body fluid and nerves existing therein are compressed, and thus the circulation of the body fluid is stagnated or pain is caused. Here, when the two tapes 11 to be affixed to the body are attached to the skin, as shown in FIG. 2C, the epidermis and dermis are raised, and the dermis, subcutaneous tissue, fascia and muscle, and the circulation vessels of body fluid and nerves existing therein are released from the compression, and the circulation of the body fluid such as blood or lymph is also improved. Consequently, the pain is reduced and the healing of the inflammation is facilitated.

FIG. 3 is a schematic view explaining a skin internal structure when three tapes to be affixed to the body in a taping kit are attached to a body. FIG. 3A shows a normal internal structure, and FIG. 3B shows a state in which the muscle causes inflammation and swells. For example, when a muscle part causes inflammation and swells, as in FIG. 1 and FIG. 2 described above, the dermis, subcutaneous tissue, fascia and muscle, and circulation vessels of body fluid and nerves existing therein are compressed, and thus the circulation of the body fluid is stagnated, or pain is caused. Here, when three tapes 11 to be affixed to the body are attached to the skin, as shown in FIG. 3C, the epidermis, dermis and fascia are raised, and thus the dermis, subcutaneous tissue, fascia and muscle, and the circulation vessels of body fluid and nerves existing therein are released from the compression, and the circulation of body fluid such as blood or lymph is also improved. Consequently, the pain is reduced and the healing of the inflammation is facilitated.

As explained above, the taping kit of the present disclosure comprises at least two tapes to be affixed to the body, and it is possible to raise stepwise the epidermis, dermis, and fascia by overlapping and attaching the desired number of the tapes to the body according to the purpose. As shown in FIGS. 1-3, it is possible to control a depth (to be raised) of stimulation by controlling the number of the tapes to be attached according to a part in which the inflammation is caused.

For example, when the tapes in the taping kit of the present disclosure are overlapped and attached to the skin after an incision such as laparotomy, craniotomy, or cosmetic surgery, the paint can be reduced after the incision and it can be expected to early recover the injury.

Also, for example, when the tapes in the taping kit of the present disclosure are overlapped and attached to a body causing muscle ache or arthralgia, various pains are reduced, and early healing effects can be expected.

Further, for example, when the tapes in the taping kit of the present disclosure are overlapped and attached to desired parts when exercise is taken, it can be expected to prevent occurrence of muscle ache, as well as blood flow to muscles is facilitated and motor functions are improved.

In addition, when the tapes in the taping kit of the present disclosure are overlapped and attached, aftereffects of injury such as bone fracture (pain, shivering, numbness, hypoactivity, and the like) are reduced, and it can be expected to stabilize and improve mild early internal diseases (early cardiac disease, and the like).

FIG. 4 is a schematic view showing tapes when a taping kit 1 according to first embodiment is attached to a body. FIG. 5 is a schematic view showing the tapes before the taping kit 1 according to the first embodiment is attached. The taping kit 1 according to the present embodiment comprises two or more tapes to be affixed to the body. Specifically, it comprises at least a first tape 11 and a second tape 12. If necessary, it is possible to increase the number of the tapes, such as a third tape 13 (see FIG. 12) and a fourth tape, according to the purpose.

As shown in FIG. 5, the tape in the taping kit 1 of the present disclosure contains at least a stretchable substrate and an adhesive layer on one surface of the substrate as in a conventional tape to be affixed to the body. Materials forming the substrate are not particularly limited, and any material which have been conventionally used in a field of the tape to be affixed to a body can be freely selected and used. For example, woven fabrics such as a cotton fabric, non-woven fabrics, knitted fabrics, paper sheets, synthetic resin films, foam sheets, polymer sheets may be used alone or as a mixture of two or more thereof. Materials having flexibility and elasticity are particularly preferable in terms of the adaptability to an adherend. Materials having air-permeability are also preferable, in order to prevent stuffiness caused by obstruction of dermal respiration.

The type of the pressure-sensitive adhesive, forming the pressure-sensitive adhesive layer, is not particularly limited, and any pressure-sensitive adhesive, which can be used for a known tape to be affixed to the body, can be freely selected and used. For example, pressure-sensitive adhesives may be used, for example, natural rubber-based, synthetic rubber-based, acrylic, urethane-based, vinyl ether-based, silicone-based, aqueous, emulsion-based, UV-based agents may be used.

The thicknesses of the substrate and the pressure-sensitive adhesive layer are not limited so long as the effects of the present invention are not impaired, and the substrate may have, for example, a thickness of 10-75 μm, and the pressure-sensitive adhesive layer may have a thickness of 1-60 μm. The form of the pressure-sensitive adhesive layer is not also particularly limited, and the substrate may have the pressure-sensitive adhesive layer on the one whole surface thereof, or may have a desired pattern formed of parts having the pressure-sensitive adhesive layer and parts having no pressure-sensitive adhesive layer, on the one surface thereof, in order to improve the air-permeability. Each tape is explained in detailed below.

(1) First Tape 11

A first tape 11 has a plurality of slits 111 in the longitudinal direction. The form of the slit 111 is not particularly limited so long as the effects of the present invention are not impaired, and can be freely designed according to the purpose.

For example, as the first tape 11 in the taping kit 1 according to the first embodiment shown in FIGS. 4 and 5, the slits 111 may be provided inside in the longitudinal direction while leaving both of the end parts in the longitudinal direction. When the slits are formed as described above, an effect of raising the skin at the central part of the tape 11 attached can be exhibited.

In addition, for example, it is also possible to provide slits 111 from the inside to one end part in the longitudinal direction except for the other end part in the longitudinal direction, as a first tape 11 in the taping kit 1 according to the second embodiment shown in FIGS. 6 and 7. When the slits are formed as described above, the skin is raised along the direction of the slits 111, and the blood and the lymph beneath the skin tissues can be made to flow more easily along the direction of the slits 111.

In addition, for example, it is also possible to provide a hole 112 at the center part and slits 111 from the hole 112 to both of the ends, as a first tape 11 in a taping kit 1 according to a third embodiment shown in FIGS. 8 and 9. When the slits are formed as described above, the skin at the center part of the tape 11 attached is raised, and, at the same time, the blood and the lymph beneath the skin tissues can be made to flow more easily along the direction of the slits 111.

(2) Second Tape 12

A second tape 12 has a plurality of slits 121 in the longitudinal direction, as the first tape 11. The form of the slit 121 is not particularly limited so long as the effects of the present invention are not impaired, and can be freely designed according to the purpose. Specific form of the slit 121 is the same as those of the slit 111 in the first tape 11, and thus the explanation thereof is omitted here.

The second tape 12 is a tape which is overlapped on at least a part of the first tape 11 and attached. A method for attaching the second tape 12 is not particularly limited so long as it is overlapped on at least a part of the first tape 11. For example, the tapes can be overlapped so that the slits 111 in the first tape 11 are crossed to the slits 121 in the second tape 12, and attached, as shown in the first embodiment in FIGS. 4 and 5 and the second embodiment in FIGS. 6 and 7. In addition, as shown in the third embodiment in FIGS. 8 and 9, it is possible to overlap the center parts and attach.

The first tape 11 and the second tape 12 may have the same form to those in the first to third embodiments in FIGS. 4-9, or it is possible to design a different form from them. For example, it is possible that the first tape 11 has a form in which slits 111 are provided inside the longitudinal direction while leaving both of the end parts in the longitudinal direction, and the second tape 12 has a form in which the slits 121 are provided from the inside to one end part in the longitudinal direction except for the other end part in the longitudinal direction, as shown in a fourth embodiment in FIGS. 10 and 11.

(3) Third Tape 13

FIG. 12 is a schematic view showing a state in which a taping kit 1 according to a fifth embodiment is attached to a body. FIG. 13 is a schematic view showing a state before the taping kit 1 according to the fifth embodiment is attached. The third tape 13 has a plurality of slits 131 in the longitudinal direction, as the first tape 11 and the second tape 12. The form of the slit 131 is not particularly limited so long as the effects of the present invention are not impaired, and can be freely designed according to the purpose. Specific form of the slit 131 is the same as those of the slit 111 in the first tape 11 and the slit 121 in the second tape 12, and the explanation thereof is omitted here.

The third tape 13 is a tape, which is overlapped on at least a part of the first tape and the second tape and is attached. A method for attaching the third tape 13 is not particularly limited so long as it is overlapped on at least a part of the first tape 11 and the second tape. Specific embodiment in which how the third tape 13 is overlapped and attached is the same as the embodiment in which the second tape 12 is overlapped and attached, and thus the explanation thereof is omitted here.

In addition, the third tape 13 may have the same form to those in the first tape 11 and the second tape 12, or it is possible to design a different form from them. Although not shown in a drawing, for example, it is possible that the first tape 11 has a form in which slits 111 are provided inside the longitudinal direction while leaving both of the end parts in the longitudinal direction. The second tape 12 has a form in which the slit 121 is provided from the inside to one end part in the longitudinal direction except for the other end part in the longitudinal direction, and the third tape 13 has a form in which the slit 131 is provided from the inside to one end part in the longitudinal direction except for the other end part in the longitudinal direction.

(4) Others

It is possible that the taping kit 1 of the present disclosure comprises, in addition to the first to third tapes described above, the desired number of tapes, such as a fourth tape and a fifth tape, if necessary. In such a case, it is possible to design so that each tape has the same form or a different form. For example, it is possible to comprise a tape T having no slits, as the third embodiment shown in FIGS. 8 and 9.

In addition, as a sixth embodiment shown in FIGS. 14 and 15, it is possible to overlap the first tape 11 to the third tape 13 and to attach, then further overlap a fourth tape 14 and a fifth tape 15, which is larger than the first tape 11 to the third tape 13, thereon and to attach. When the tapes are attached as described above, for example, an effect in which the first tape 11 to the third tape 13 reduce the pain of the skin, and the fourth tape 14 and the fifth tape 15 reduce the swelling can be expected.

<Method for Attaching Tape to be Affixed to Body>

The method for attaching the tape to be affixed to the body of the present disclosure is a method comprising at least a first attaching step in which the first tape 11 is attached to an affected part; and a second attaching step in which the second tape 12 is overlapped and attached on at least a part of the first tape 11. If necessary, it is possible to perform attaching steps in times corresponding to the number of tapes, for example, a fourth attaching step in which the fourth tape 14 is attached, a fifth attaching step in which a fifth tape is attached, which is not shown in a drawing, and the like.

The form of each tape used in the method for attaching a tape to be affixed to the body of the present disclosure, and the method for overlapping and attaching each tape are the same as the methods in the taping kit of the present disclosure described above, and thus the explanations thereof are omitted here.

EXAMPLES

Experimental Example 1

In Experimental Example 1, influences obtained by using the taping kit according to the present disclosure to patients after an incision were examined.

Specifically, 39 patients, who had median sternotomy by a heart-thoracic surgical procedure, were randomly divided into a group of 23 patients to who the tape was attached and a group of 16 patients to who the tape was not attached using Microsoft Excel, and the tape was attached in a method shown in the photograph that substitutes for a drawing of FIG. 16. Follow-up about a pain value, an amount of opioid analgesic used, an amount of paracetamol (analgesic) used, a subjective symptom of respiratory distress, and a degree of pain was investigated from the first day to the eighth day. The pain value was evaluated so that the evaluation was decided as 0 if a patient felt no pain in a range of 0-10, and the larger the number, the stronger the pain. Note that specific backgrounds of the subjects are shown in Table 1 below. The results are shown in FIGS. 17-21.

TABLE 1

|  |  | Tape | no tape | p-Value |
| --- | --- | --- | --- | --- |
| Number (n) |  | 23 | 16 |  |
| Age |  | 66 ± 9 | 67 ± 8 | 0.83 |
| Gender | Female | 5 (22%) | 1 (5%) | 0.75 |
|  | Male | 18 (78%) | 15 (95%) |  |
| Vavular aortic stenosis |  | 2 (9%) | 3 (19%) | 0.63 |
| Coronary |  | 20 (87%) | 10 (63%) | 0.12 |
| Sternum dehiscence |  | 1 (4%) | 0 (0%) | 1.0 |
| Aneurysm |  | 0 (0%) | 1 (6%) | 0.41 |
| Paravalvular abscess |  | 0 (0%) | 1 (6%) | 0.41 |
| Mitral valve calcification |  | 0 (0%) | 1 (6%) | 0.41 |
| Aortic valve insufficiency |  | 0 (0%) | 1 (6%) | 0.41 |

FIG. 17 is a graph that substitutes for a drawing showing the results of the pain value. A number in each group is an average value. As shown in FIG. 17, the pain values obtained in the group in which the tape was used were lower than those obtained in the group in which the tape was not used in all days of the first day to the eighth day. In addition, the pain values obtained in the group in which the tape was used were lower with the significant difference than those obtained in the group in which the tape was not used on the second day to the sixth day.

FIG. 18 is a graph that substitutes for a drawing showing the results of the amount of the opioid analgesic used. A number in each group is an average value. As shown in FIG. 18, the amounts of the opioid analgesic used in the group in which the tape was used were smaller than those used in the group in which the tape was not used on the first day to the fourth day. In addition, the amounts of the opioid analgesic used in the group in which the tape was used were smaller with the significant difference than those used in the group in which the tape was not used on the first day and the fourth day.

FIG. 19 is a graph that substitutes for a drawing showing the results of the amount of the paracetamol (analgesic) used. A number in each group is an average value. As shown in FIG. 19, the amounts of the paracetamol (analgesic) used in the group in which the tape was used were smaller than those used in the group in which the tape was not used on the first day to the seventh day. In addition, the amounts of the paracetamol (analgesic) used in the group in which the tape was used were smaller with the significant difference than those used in the group in which the tape was not used on the second day.

FIG. 20 is a graph that substitutes for a drawing showing the number of occurrences of a subjective symptom of respiratory distress. As shown in FIG. 20, 14 patients of the 16 patients complained of the respiratory distress in the group in which the tape was not used, and 5 patients of the 23 patients complained of the respiratory distress in the group in which the tape was used. In addition, with respect to the number of patients who did not complained of the respiratory distress in each group, the results show that the number in the group in which the tape was used was larger with the significant difference than that in the group in which the tape was not used.

FIG. 21 is a graph that substitutes for a drawing showing the number of the patients when a degree of pain is divided into 6 classes. As shown in FIG. 21, it was understood that the number of the patients having strong pain was larger in the group in which the tape was not used, and the number of the patients having slight pain was larger in the group in which the tape was used. The results show that the number of the patients having slight pain in the group in which the tape was used was larger with the significant difference than that in the group in which the tape was not used, and the number of the patients having very strong pain in the group in which the tape was not used was larger with the significant difference than that in the group in which the tape was used.

From the results described above, it could be confirmed that the symptoms such as the pain or respiratory distress after an incision were lessened and an effect of facilitating early recovery was obtained by using the taping kit according to the present disclosure.

Experimental Example 2

In Experimental Example 2, influences obtained by using the taping kit according to the present disclosure for a patient with early atrial contraction were examined.

Specifically, tapes were attached in methods shown in photographs that substitutes for a drawing in FIGS. 22-25 to a 61-aged male complaining of irregular heartbeats and pains expanding from the waist and back to the cervical region and occipital. As a results, the cardiac rate was reduced and the pains in various places were relieved.

From the results described above, it was suggested that the mild early cardiac disease could be stabilized and improved by using the taping kit according to the present disclosure.

Experimental Example 3

In Experimental Example 3, influences obtained by using the taping kit according to the present disclosure for a patient with aftereffect after bone fracture were examined.

Specifically, tapes were attached in methods shown in photographs that substitutes for a drawing in FIGS. 26 and 27 to a 37-aged male complaining of symptoms such as shivering of a wrist, hypoactivity, and insensitivity after bone fractures of ulna and radius in a right hand. As a result of a written examination carried out after 5 weeks from beginning of the attachment, as shown in FIG. 28, a writing pressure was improved, and a quality of writing of straight lines and curved lines were also improved.

From the results described above, it was suggested that the various aftereffects caused after the bone fractures could be relieved by using the taping kit according to the present disclosure.

The invention claimed is:

1. A method for attaching tapes to be affixed to a body, which contains at least a stretchable substrate and an adhesive layer on one surface of the substrate, the method comprising:
   a first attaching step in which a first tape, which has a first hole at a center part of the first tape and a plurality of slits formed from a vicinity of the first hole to an end part of the first tape in a longitudinal direction, and wherein the plurality of slits is not formed in a middle area of the first tape including the first hole, is attached to an affected part; and
   a second attaching step in which a second tape, which has a second hole at a center part of the second tape and a plurality of slits formed from a vicinity of the second hole to an end part of the second tape in the longitudinal direction, and wherein the plurality of slits is not formed in a middle area of the second tape including the second hole,
   wherein the second attaching step includes a step of overlapping the second hole of the second tape with the first hole of the first tape, and attaching the middle area of the first tape and the middle area of the second tape each other.

2. The method for attaching tapes according to claim 1, wherein the affected part is on a skin after an incision.

* * * * *